United States Patent
Fletter

(10) Patent No.: US 11,253,675 B2
(45) Date of Patent: Feb. 22, 2022

(54) URINARY CATHETER WITH SEALED CHAMBER AND METHOD

(71) Applicant: Hollister Incorporated, Libertyville, IL (US)

(72) Inventor: Paul C. Fletter, Mt. Prospect, IL (US)

(73) Assignee: Hollister Incorporated, Libertyville, IL (US)

( * ) Notice: Subject to any disclaimer, the term of this patent is extended or adjusted under 35 U.S.C. 154(b) by 396 days.

(21) Appl. No.: 16/313,563

(22) PCT Filed: Jun. 29, 2017

(86) PCT No.: PCT/US2017/039979
§ 371 (c)(1),
(2) Date: Dec. 27, 2018

(87) PCT Pub. No.: WO2018/005783
PCT Pub. Date: Jan. 4, 2018

(65) Prior Publication Data
US 2019/0151610 A1    May 23, 2019

Related U.S. Application Data

(60) Provisional application No. 62/356,295, filed on Jun. 29, 2016.

(51) Int. Cl.
*A61M 25/00* (2006.01)
*A61M 27/00* (2006.01)
(Continued)

(52) U.S. Cl.
CPC ......... *A61M 25/0017* (2013.01); *A61F 5/451* (2013.01); *A61M 25/002* (2013.01);
(Continued)

(58) Field of Classification Search
CPC . A61F 5/451; A61M 25/0017; A61M 25/002; A61M 25/0097; A61M 27/008; A61M 39/22
See application file for complete search history.

(56) References Cited

U.S. PATENT DOCUMENTS

| | | |
|---|---|---|
| 3,361,253 A | 1/1968 | Lonholdt |
| 3,959,948 A | 6/1976 | Fowler et al. |

(Continued)

FOREIGN PATENT DOCUMENTS

WO    20060990306 A2    9/2006

OTHER PUBLICATIONS

International Search Report and Written Opinion of the International Search Authority for PCT Application No. PCT/US2017/039979, dated Nov. 27, 2017.

*Primary Examiner* — Benjamin J Klein
(74) *Attorney, Agent, or Firm* — Cook Alex Ltd.

(57) ABSTRACT

A urinary catheter (20) includes a shaft (22) having a hydrophilic material and a distal end and a proximal end with a lumen running between the two. The proximal end includes an eyelet (24) that is in fluid communication with the lumen. A handle is attached to the distal end of the shaft and includes a first grip member (28) and a second grip member (32) configured so that the first grip member pivots relative to the second grip member. A sleeve (34) defines an interior chamber (45), and the shaft is positioned within the interior chamber. The sleeve is sealed to the first grip member so that when the first grip member is pivoted, the sleeve is torn open.

23 Claims, 8 Drawing Sheets

(51) Int. Cl.
*A61M 39/22* (2006.01)
*A61F 5/451* (2006.01)

(52) U.S. Cl.
CPC ...... *A61M 25/0097* (2013.01); *A61M 27/008* (2013.01); *A61M 39/22* (2013.01)

(56) References Cited

U.S. PATENT DOCUMENTS

| | | |
|---|---|---|
| 3,968,876 A | 7/1976 | Brookfield |
| 4,453,936 A | 6/1984 | Casson |
| 4,752,288 A | 6/1988 | Hussey |
| 4,846,344 A | 7/1989 | Bala |
| 5,217,114 A | 6/1993 | Gadberry et al. |
| 5,447,231 A | 9/1995 | Kastenhofer |
| 5,497,601 A | 3/1996 | Gonzalez |
| 7,476,223 B2 | 1/2009 | McBride |
| 7,571,804 B2 | 8/2009 | Kjellmann Bruun et al. |
| 8,398,615 B2 | 3/2013 | Torstensen et al. |
| 8,919,553 B2 | 12/2014 | Murray et al. |
| D734,165 S | 7/2015 | Kearns et al. |
| 9,585,784 B2 | 3/2017 | Matthiassen et al. |
| 2001/0001443 A1* | 5/2001 | Kayerod ............ A61M 25/002 206/364 |
| 2005/0090779 A1* | 4/2005 | Osypka ............ A61M 25/0097 604/160 |
| 2009/0000970 A1 | 1/2009 | Bordeau et al. |
| 2010/0258568 A1* | 10/2010 | Frederiksen ........ A61M 25/002 220/502 |
| 2012/0130329 A1 | 5/2012 | March et al. |
| 2012/0316515 A1 | 12/2012 | Terry |
| 2013/0264227 A1 | 10/2013 | Frojd |
| 2013/0338624 A1* | 12/2013 | Mansour ............ A61M 39/223 604/500 |
| 2014/0194841 A1 | 7/2014 | Matthiassen et al. |
| 2015/0238726 A1 | 8/2015 | Terry |
| 2015/0306351 A1* | 10/2015 | Bornhoft ............ A61M 25/065 604/164.01 |

* cited by examiner

URINARY CATHETER WITH SEALED CHAMBER AND METHOD

RELATED APPLICATIONS

The present application is the U.S. National Stage of a PCT International Patent Application No. PCT/US2017/039979, filed Jun. 29, 2017, which claims the benefit of and priority to U.S. Patent Application No. 62/356,295, filed on Jun. 29, 2016, the contents of both which are hereby incorporated herein by reference.

FIELD OF THE DISCLOSURE

The present disclosure relates generally to urinary catheters and, in particular, to a urinary catheter with a chamber that provides a sealed environment for the catheter.

BACKGROUND

Catheters are used to treat many different types of medical conditions and typically include an elongated shaft that is inserted into and through a passageway or lumen of the body. Urinary catheters, and in particular intermittent urinary catheters, are commonly used by those who suffer from various abnormalities of the urinary system, such as urinary incontinence. With the advent of intermittent urinary catheters, individuals with urinary system abnormalities can self-insert and self-remove catheters several times a day.

Urinary catheters typically include a shaft that is sufficiently flexible to navigate the curves of the urethra (especially catheters intended for male users), yet rigid enough to be pushed through the urethra without collapsing or "snaking" before an end of the catheter reaches the bladder. A distal end of the catheter (the end inserted into the urethra) includes draining holes or eyelets for the drainage of bodily fluids therethrough and into an internal conduit or lumen of the catheter. The proximal end of the catheter (the end grasped by the user) typically includes a handle with a connecting member, such as a funnel, for fluidly connecting the catheter to a collection container, such as a collection bag into which urine drains.

Urinary catheters for draining the bladder through the urethra are commonly packaged in a sterile and pre-lubricated condition in containers. More specifically, the shaft of the catheter is typically provided with a hydrophilic coating that provides the shaft with a lubricated surface in the presence of a hydration source. As a result, the container must provide the shaft of the catheter with a sterile, hydration environment. Oftentimes the catheters are intended to be fully removed from such containers at the time of catheterization.

The containers for catheters are often molded of a rigid or semi-rigid material and enclose the catheter shaft as well as a pre-attached urine collection bag. Such an arrangement is disclosed in U.S. Patent Application Publication No. US 2014/0194841 A1 to Matthiassen et al., and results in bulky packaging which takes up an undesirable amount space during storage and carrying.

In packaging where sealed flexible containers are used, a user may experience difficulty in tearing open the container, both in terms of the effort required and consistency in properly tearing the container to permit removal of the catheter.

The urinary catheter with hydration chamber of the present disclosure addresses at least some of the above issues.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a urinary catheter includes a shaft including a hydrophilic material and a distal end and a proximal end with a lumen running therebetween. The proximal end includes an eyelet in fluid communication with the lumen. A handle is attached to the distal end of the shaft, and the handle includes a first grip member and a second grip member configured so that said first grip member pivots relative to the second grip member. A sleeve defining an interior chamber is sealed to the first grip member with the shaft positioned within the interior chamber. When the first grip member is pivoted, the sleeve is torn open. Optionally, a hydration source also may be positioned within the interior chamber of the sleeve.

In another aspect, a urinary catheter includes a shaft including a hydrophilic material and a distal end and a proximal end with a lumen running therebetween. The proximal end includes an eyelet in fluid communication with the lumen. A handle is attached to the distal end of the shaft. The handle includes a first grip member with a first internal passage therethrough and a second grip member with a second internal passage therethrough. The first or second internal passage is in fluid communication with the lumen of the shaft. The first and second grip members are configured so as to pivot relative to each other between a closed configuration, where the first and second internal passages are not in fluid communication, and an open configuration, where the first and second internal passages are in fluid communication. A sleeve includes a sealed interior chamber with the shaft positioned within the interior chamber. Optionally, a hydration source also may be positioned within the interior chamber of the sleeve.

In yet another aspect, a method is disclosed for providing a sealed chamber for a catheter shaft, where the shaft has a lumen therethrough and the catheter has a handle having a valve in fluid communication with the lumen. The method includes positioning the shaft of the catheter in a chamber of a sleeve, sealing the sleeve to the handle and closing the valve so as to prevent fluid communication of the catheter lumen with an ambient environment outside of the chamber of the sleeve.

DETAILED DESCRIPTION OF EMBODIMENTS

Figure 1:
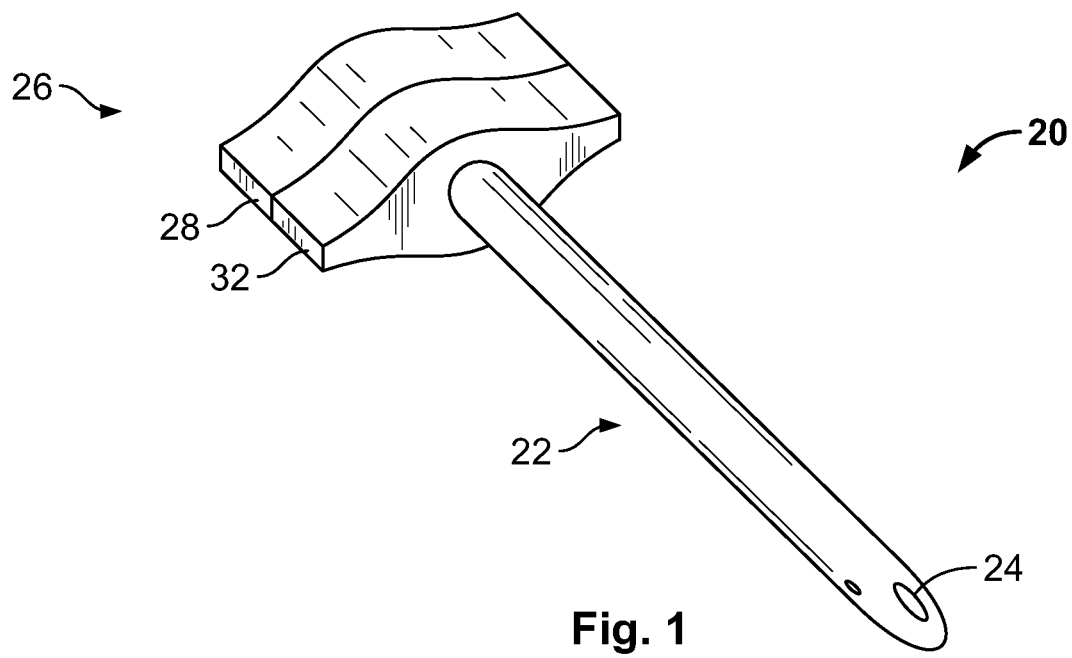
FIG. 1 is a perspective view of a catheter prior to being packaged in accordance with an embodiment of the present disclosure.

An intermittent catheter in a first embodiment of the present disclosure is indicated in general at 20 in FIG. 1. The catheter features a tubular shaft, indicated in general at 22, having a central lumen in fluid communication with one or more eyelets 24 formed in the proximal end. The shaft is constructed from hydrophilic material or is provided with a hydrophilic coating, as is known in the art, so that it features a lubricated surface when exposed to a moist or humid environment. The distal end of the shaft 22 is attached to a handle, indicated in general at 26. The handle features a distal grip member 28 and a proximal grip member 32. As an example only, the proximal and distal grip members may be constructed from molded plastic.

The terms "distal" and "proximal" are used throughout this disclosure. When used in the context of the catheter tube or shaft that is inserted into the body of the user, the term "proximal" is used to refer to that end or portion of the catheter shaft that, during use, is closer in proximity to the user's body and/or initially enters the user's body upon insertion. The term "distal" is used to refer to an end or portion of the catheter shaft that is opposite the proximal end or portion and is typically further away from the user's body. For the sake of consistency, when the terms "distal" and "proximal" are used in the context of a housing or member that receives or carries the catheter tube such as the handle or grip members, which are not intended for introduction into the user's body, a proximal end or proximal portion is that end or portion closer to the proximal end of the catheter shaft when the catheter shaft is housed or carried by such housing or member, while the distal end or portion is located opposite to such proximal end or portion.

Figure 2:
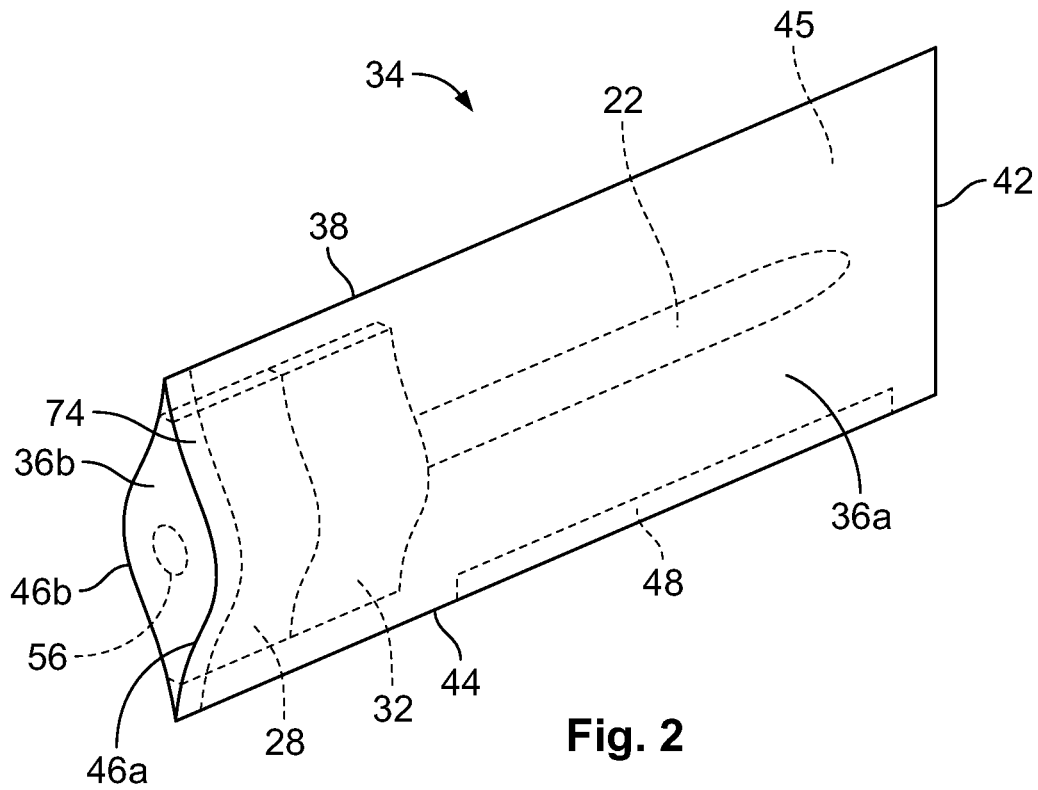
FIG. 2 is a perspective view of a sleeve for providing a hydration chamber for the catheter of FIG. 1 in accordance with an embodiment of the present disclosure.
Figure 3:
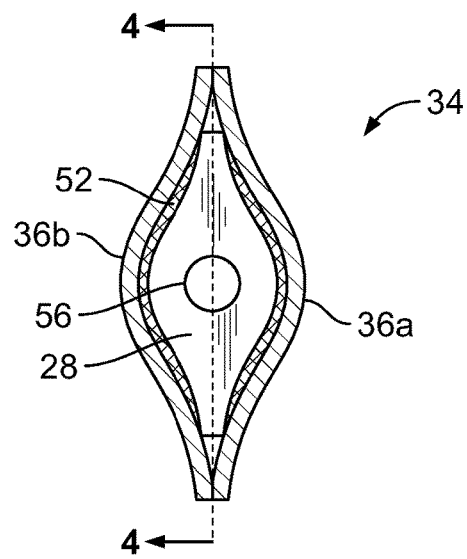
FIG. 3 is an end elevational view of the catheter of FIG. 1 after being packaged within the sleeve of FIG. 2 in accordance with an embodiment of the present disclosure.

A package in the form of a pouch or sleeve is indicated in general at 34 in FIGS. 2 and 3. It preferably is constructed from panels 36a and 36b that are sealed together along edges 38, 42 and 44 (FIG. 2), such as by welding or adhesive, so that an interior chamber 45 is defined. With reference to FIG. 2, edge portions 46a and 46b of the panels define an open end of the sleeve 34.

The panels 36a and 36b, and thus the sleeve 34, may be constructed from a liquid and vapor impermeable material that retains both liquids and vapors and that may be torn to open. As an example only, the material may be foil, plastic or a laminate (which may or may not be transparent).

Figure 4:
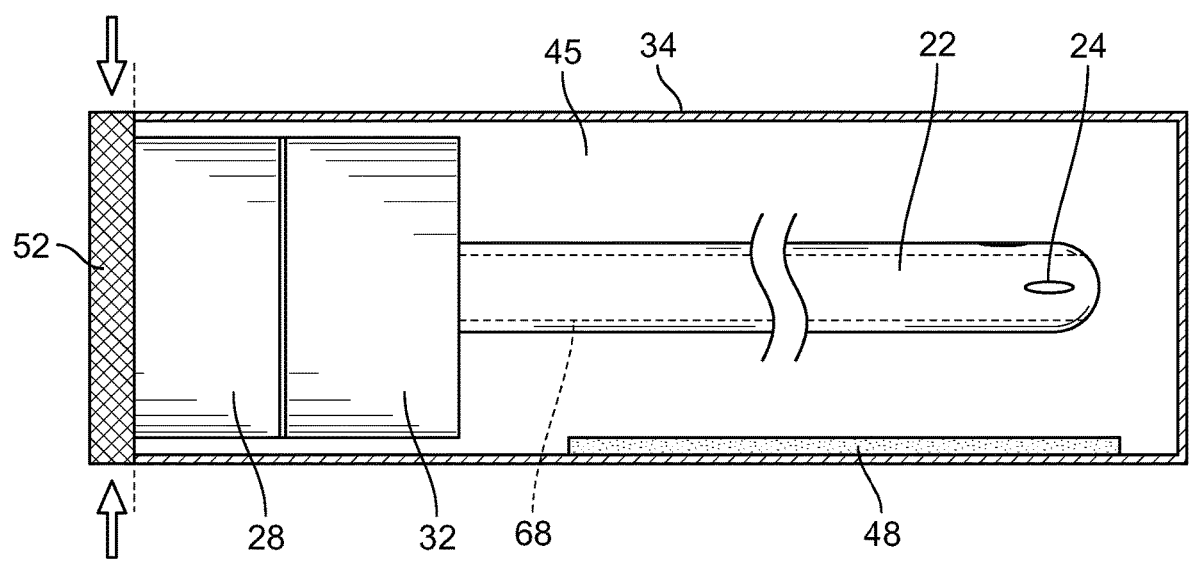
FIG. 4 is a partial sectional, side elevational view of the catheter and sleeve of FIGS. 1-3 with a cross sectional view of the sleeve taken along line 4-4 of FIG. 3.

As illustrated in FIGS. 2-4, the intermittent catheter of FIG. 1 is positioned within the interior chamber of the sleeve 34. In addition, a hydration or vapor source or media (48 in FIGS. 2 and 4) is positioned within the interior chamber of the sleeve. As an example only, the hydration media may be water or saline, but other suitable hydration sources and media are well known in the art and may be used instead. In one embodiment, the hydration source may be liquid water in direct contact with the hydrophilic material of the catheter. In another embodiment, the hydration source may be a vapor hydration source that includes liquid that donates a vapor to produce a vapor hydration atmosphere within the sealed interior chamber. The vapor donating liquid may be sequestered in an absorbent material and/or in a chamber made from a vapor permeable liquid impermeable barrier.

As shown in FIGS. 3 and 4, the end portions of the sleeve 34 that define the end opening of the sleeve are secured and sealed to the distal grip member 28 of the handle so that seal 52 is formed. This may be accomplished by welding, adhesive or any other securing and sealing arrangement and/or method known in the art.

As a result, the sleeve 34 serves as a sterile liquid and vapor barrier and the interior chamber 45 becomes a sterile, sealed hydration chamber.

Figure 5:
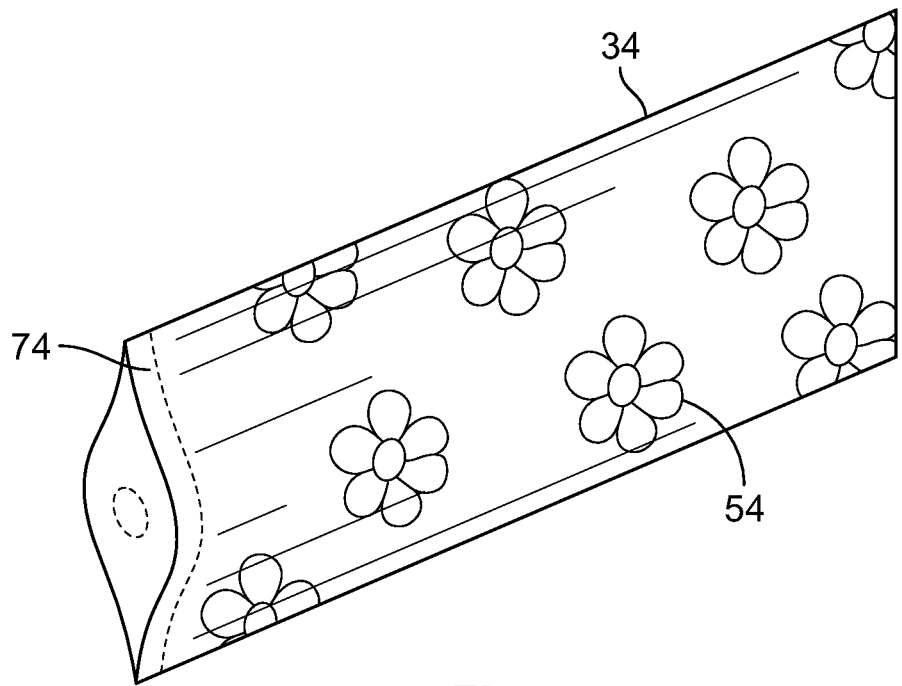
FIG. 5 is a perspective view of an alternative embodiment of the sleeve of FIG. 2.

As illustrated in FIG. 5, the exterior surface of the sleeve 34 may be provided with a decorative or artistic pattern 54 so that the product does not appear to be a "medical" type of product, thus helping to ensure the user's privacy. As an example only, the product could be feature a pattern 54 that provides the appearance of a travel-sized bottle of lotion.

As shown in FIGS. 2 and 3, the distal grip member 28 of the handle includes an opening 56 that communicates with the lumen of the shaft 22, and thus shaft eyelets 24. During use of the catheter, urine enters the eyelet(s) at the distal tip of the catheter, flows through the catheter lumen and a passage through the handle and out through the opening 56 into a toilet or other container or disposal destination. As a result, the opening 56 must be closed, that is, the luminal pathway shutoff, to retain the moist vapor within the interior chamber of the sleeve and to prevent the loss of hydration media through evaporation/diffusion over time (so as to extend the product's shelf life). In accordance with the present disclosure, this is accomplished by plugging, covering, or occluding the luminal pathway. As will now be explained, a valve may be provided in the handle of the catheter for this purpose.

Figure 6:
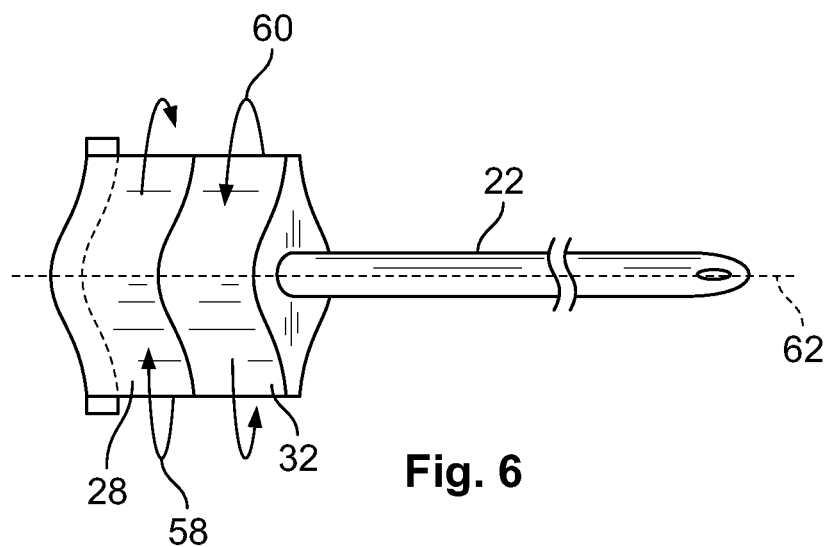
FIG. 6 is a perspective view of the catheter of FIG. 1 illustrating opening and closing the handle valve of the catheter.

As shown by arrows 58 and 60 in FIG. 6, distal and proximal grip portions 28 and 32 may be mounted so that they pivot about a longitudinal axis of the catheter (indicated at 62) with respect to the catheter shaft 22. Alternatively, proximal grip portion 32 may be mounted to the catheter shaft 22 in a fixed fashion with distal grip portion 28 pivotally mounted thereto. In either arrangement, the grips effectively pivot with respect to one another.

Figure 7A:
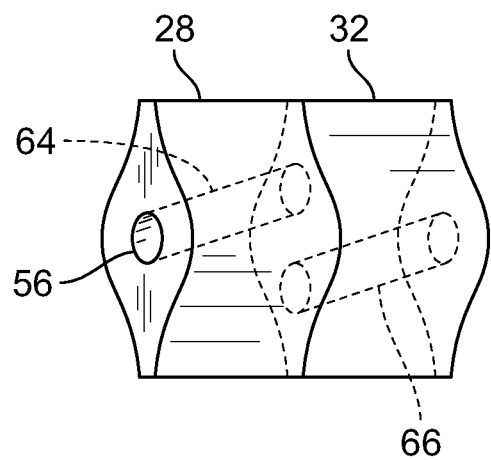
FIGS. 7A and 7B are transparent perspective views of a first embodiment of the handle valve of the catheter of FIG. 6 in the closed and open configurations, respectively.
Figure 7B:
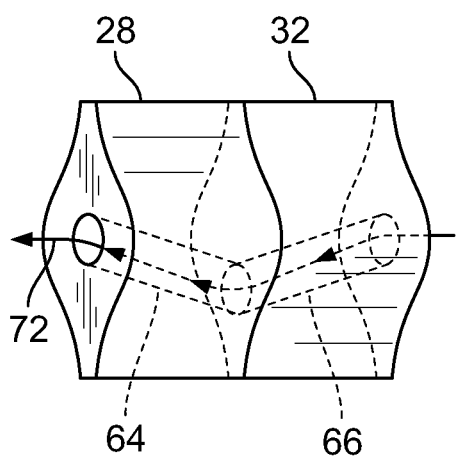

As illustrated in FIGS. 7A and 7B, the distal and proximal grip members 28 and 32 may be provided with internal passages 64 and 66, respectively. The distal end of passage 64 corresponds to opening 56 of the distal grip, while the proximal end of passage 66 is in communication with the lumen (shown at 68 in phantom in FIG. 4) of the catheter shaft. As a result, the distal and proximal grip members 28 and 32 of the catheter handle together form a shutoff valve that is opened and closed with a twisting method. More specifically, when the proximal and distal gripping members are positioned as illustrated in FIG. 7A, the handle valve is in a closed configuration so that the catheter lumen, and thus the interior chamber of the sleeve (34 of FIG. 4) is not in fluid communication with the external environment. To place the catheter in a configuration for use, the user pivots the distal and proximal grip members with respect to one another (arrows 58 and 60, or just arrow 58, of FIG. 6) so that the passages 64 and 66 are placed in fluid communication, as illustrated in FIG. 7B. Fluid is then free to flow from the lumen of the catheter shaft through the passages, as illustrated by arrows 72 of FIG. 7B.

Figure 8A:
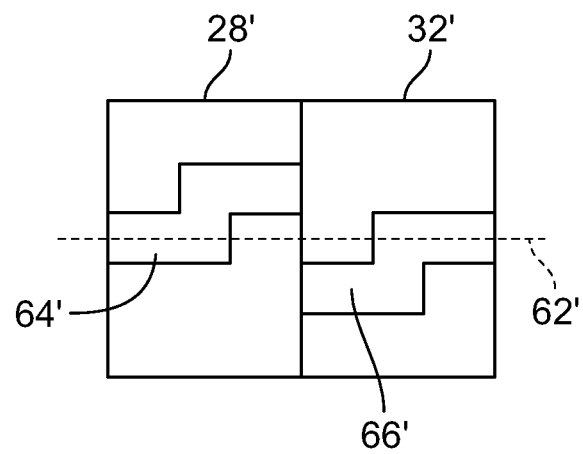
FIGS. 8A and 8B are transparent side elevational views of a second embodiment of the handle valve of the catheter of FIG. 6 in the closed and open configurations, respectively.
Figure 8B:
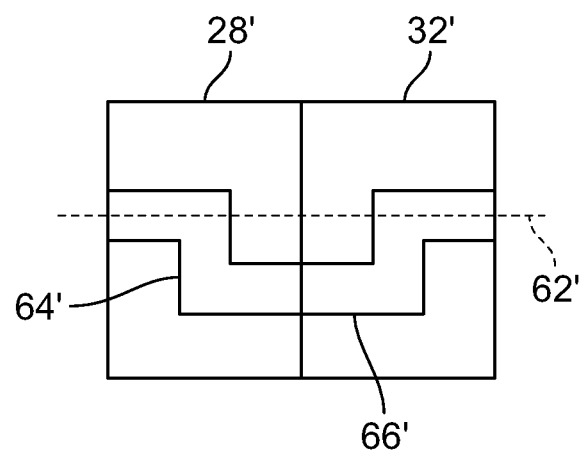

An alternative arrangement of the internal passages of the distal and proximal grip members is illustrated in FIGS. 8A and 8B, where the distal and proximal members are indicated at 28' and 32', the passages are indicated at 64' and 66' and the pivot axis for the grip members is indicated at 62'. The handle valve is illustrated in the closed configuration in FIG. 8A and in the open configuration in FIG. 8B.

In alternative embodiments, the passages of the proximal and distal grip members may take alternative forms. In still additional embodiments, the twisting motion of the handle valve may alternatively break a frangible seal or otherwise open a sealing member that seals the fluid path or passage(s) through the grip members.

Figure 9A:
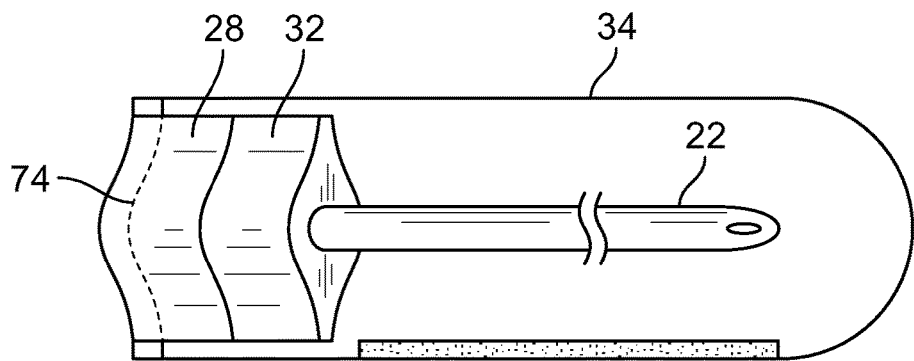
FIGS. 9A-9C are perspective views illustrating removal of the catheter from the sleeve of FIGS. 2-4, with FIG. 9A illustrating the catheter and sleeve in an initial storage configuration, FIG. 6B illustrating sleeve being opened and FIG. 6C illustrating the catheter being withdrawn from the sleeve.
Figure 9B:
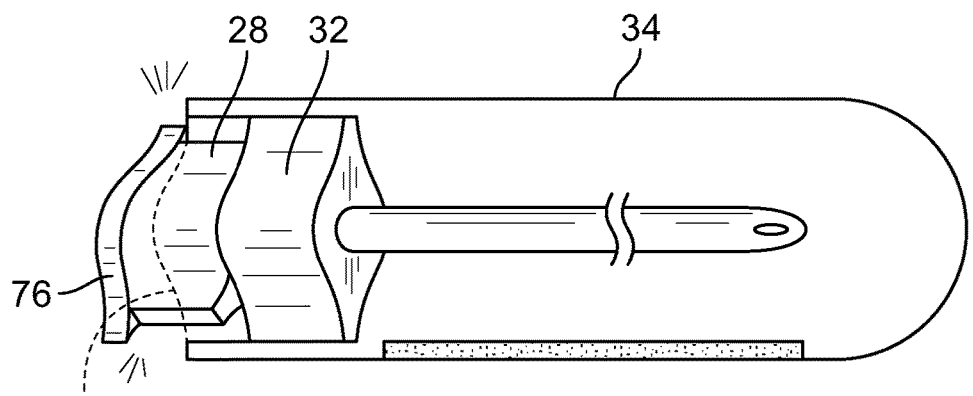
Figure 9C:
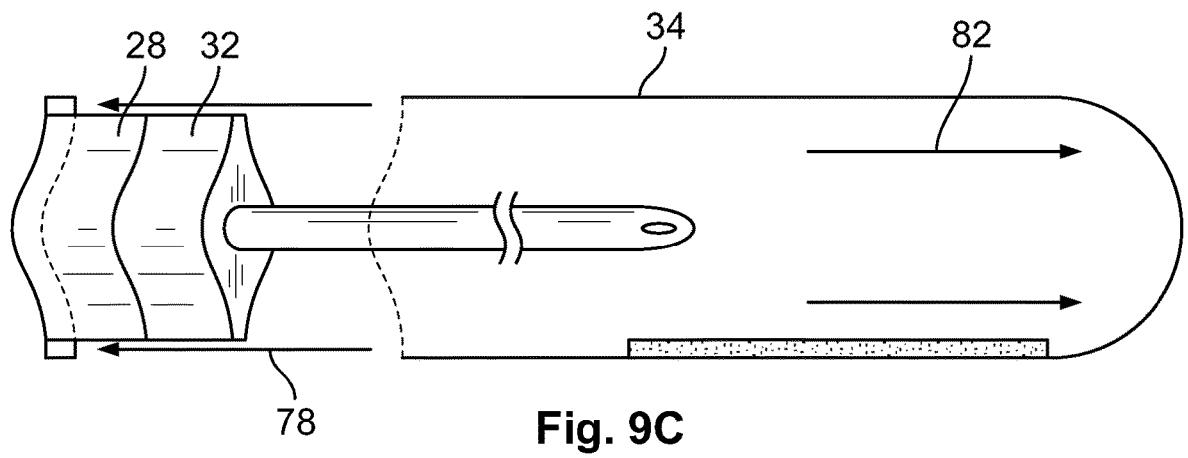

As illustrated in FIGS. 9A-9C, the twisting motion that opens the handle valve also tears the sleeve open along a tear line 74 (also shown in FIGS. 2 and 5), which is preferably perforated. More specifically, the packaged intermittent catheter is illustrated in a storage configuration in FIG. 9A. As shown in FIG. 9A, the catheter shaft 22 and distal and proximal grip members 28 and 32 are positioned within sleeve 34 and a sealed hydration environment is provided therein. The grip members 28 and 32 are in alignment with one another with their internal passages positioned as illustrated in FIG. 7A (or 8A) so that the handle valve is in the closed configuration.

To remove the catheter from the sleeve 34, the user grips the proximal grip member 32 (through the sleeve 34) with one hand and grips and pivots distal grip member 28, as illustrated in FIG. 9B, using the other hand. This causes the sleeve to tear open along tear line 74 as the portion 76 of the sleeve attached to the distal grip member pivots with it and is torn away from the remaining portion of the sleeve.

It should be noted that the twist-handle arrangement of the illustrated embodiment provides leverage to make opening of the packaging (sleeve) easier and more repeatable along the tear line 74.

The user continues to rotate the distal grip member 28 of the handle until it is in the position illustrated in FIG. 9C. As a result, the distal and proximal grip members 28 and 32 have been rotated 180° with respect to one another and the internal passages of the grip members are configured as illustrated in FIG. 7B (or 8B) so that the handle valve is in the open configuration. In addition, the user is free to remove the catheter from the sleeve, as indicated by arrows 78 and 82. Of course, the user is free to remove the catheter from the sleeve any time after the sleeve has been torn along tear line 74 (i.e. any time after the step illustrated in FIG. 9B)—the user may continue to twist the grip members into the position illustrated in FIG. 9C after the catheter is removed from the sleeve.

In alternative embodiments, the internal passages or lumen pathway seal may be configured such that a grip member requires less than 180° or pivoting or rotation to place the handle valve in the open configuration.

In embodiments wherein a shutoff valve is not incorporated into the proximal and distal grip members, one or both of the members may still be pivotally mounted with respect to the catheter so that the sleeve is still torn along tear line 74 when one or both of the grip members is pivoted.

While the embodiments of the intermittent catheter illustrated above are configured to drain urine into a toilet or other disposal container or destination, the catheter may be easily modified to include a urine collection bag to provide a closed system. More specifically, the twist-handle shutoff valve feature allows a closed-system collection bag to be pre-attached to the catheter assembly during manufacturing without compromising the hydration chamber package. The handle valve prevents vapor from reaching the bag via the intraluminal pathway so as to prevent the loss of hydration media through the bag material (due to the moisture vapor transmission rate of the bag material).

Figure 10:
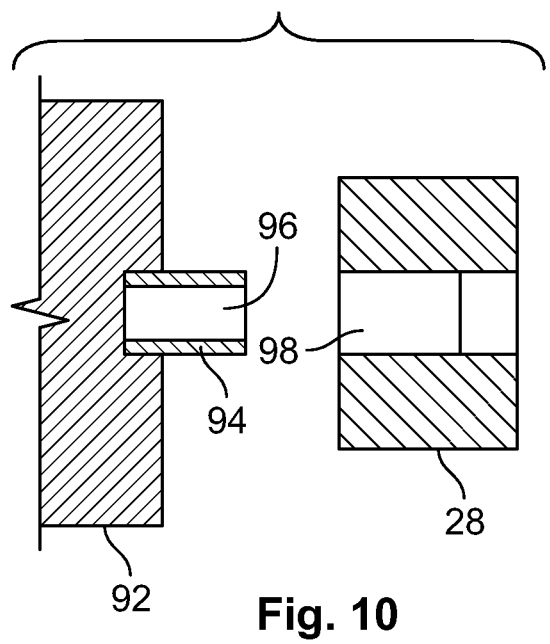
FIG. 10 is a schematic view illustrating a method of attaching a collection bag to the catheter of FIGS. 9A-9C.

With reference to FIG. 10, a collection bag 92 is provided with a cylindrical connector 94 having a central bore 96 that is in fluid communication with the interior of the bag. The connector 94 is preferably constructed from a material that is at least semi-rigid (such as, as an example only, plastic). The distal grip member 28 features an internal passage 98 that is sized to receive the connector 94. The connector may be secured within the passage 98 by adhesive, a barb arrangement, interference fit or any other suitable, sealing attachment arrangement known in the art. As a result, the collection bag 92 is secured to the distal grip member 28 of the catheter, as illustrated in FIGS. 12A-12D.

Figure 11:
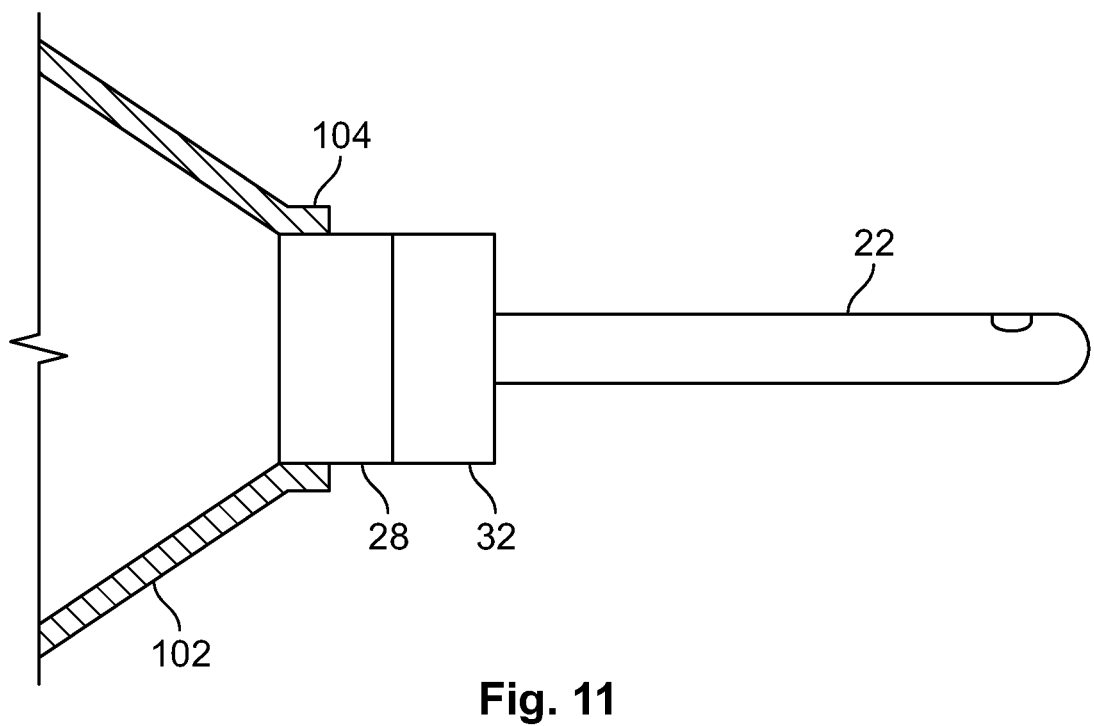
FIG. 11 is a side elevational view of the catheter of FIG. 6 and a cross-sectional view of a collection bag illustrating an alternative method of attaching the collection bag to the catheter.

In an alternative embodiment, illustrated in FIG. 11, the collection bag 102 may include an opening surrounded by edge portions 104 of the bag that are directly secured to, and sealed against, the distal grip member 28. The collection bag may be attached and sealed to the distal grip member 28 by adhesive, welding or any other suitable attachment arrangement known in the art.

Figure 12A:
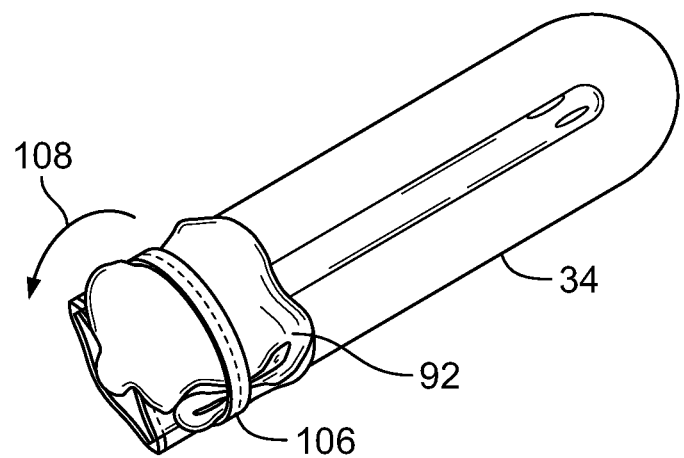
FIGS. 12A-12D are perspective views illustrate deployment of the fluid collection bag in a second embodiment of the catheter of the disclosure, with FIG. 12A illustrating the catheter, bag and sleeve in an initial storage configuration, FIG. 12B illustrating the bag after release from the pouch and being unrolled, FIG. 12C illustrating the unrolled bag prior to the wings of the bag being unfolded and FIG. 12D illustrating the bag of FIG. 12C after the wings of the bag have been unfolded.
Figure 12B:
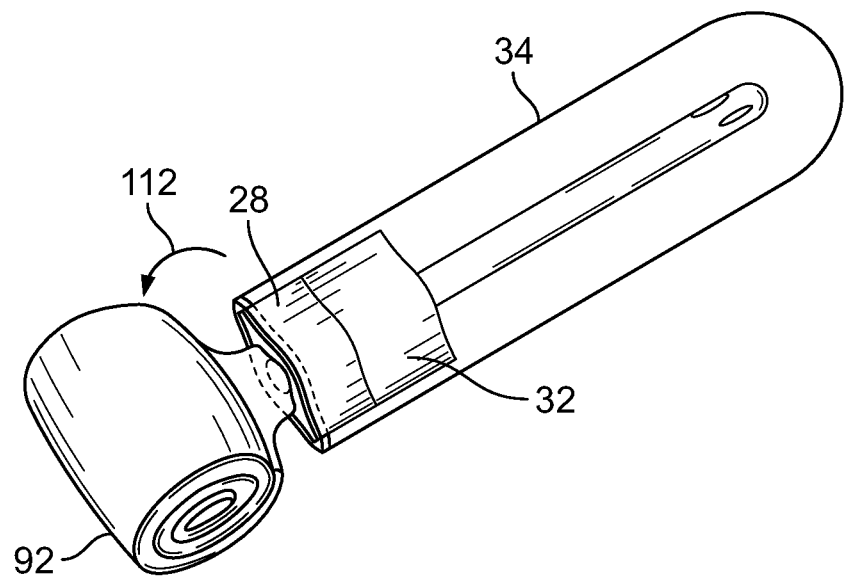

As illustrated in FIG. 12A, the collection bag 92 of FIG. 10 (or collection bag 102 of FIG. 11) may be folded and secured to the sleeve 34 by a retaining member, such as a band 106, which is preferably made of an elastic material, to provide a compact storage profile. The handle valve of the catheter is in the closed configuration, such as is illustrated in FIG. 7A or 8A.

When an individual wishes to use the catheter, the band is removed and the bag is unfolded away from the sleeve 34, as illustrated by arrow 108 of FIG. 12A. Next the collection bag 92 is unrolled, as illustrated by arrow 112 of FIG. 12B and arrows 114 of FIG. 12C.

Figure 12C:
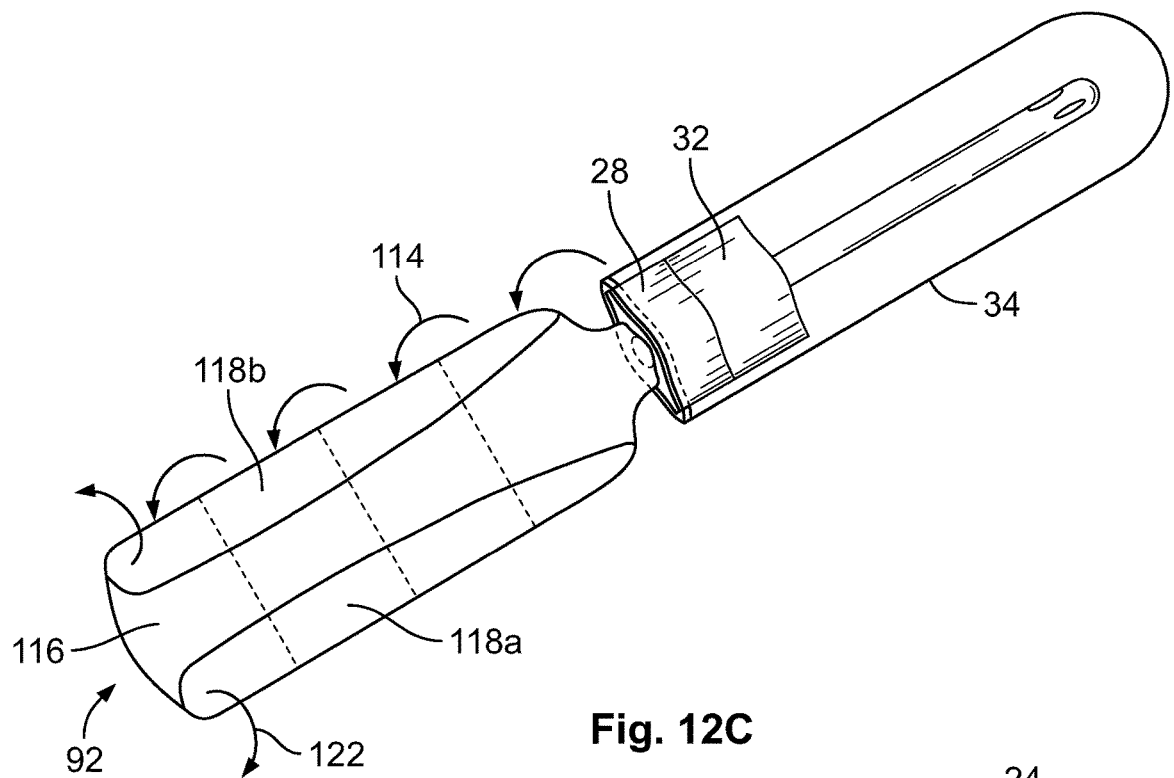
Figure 12D:
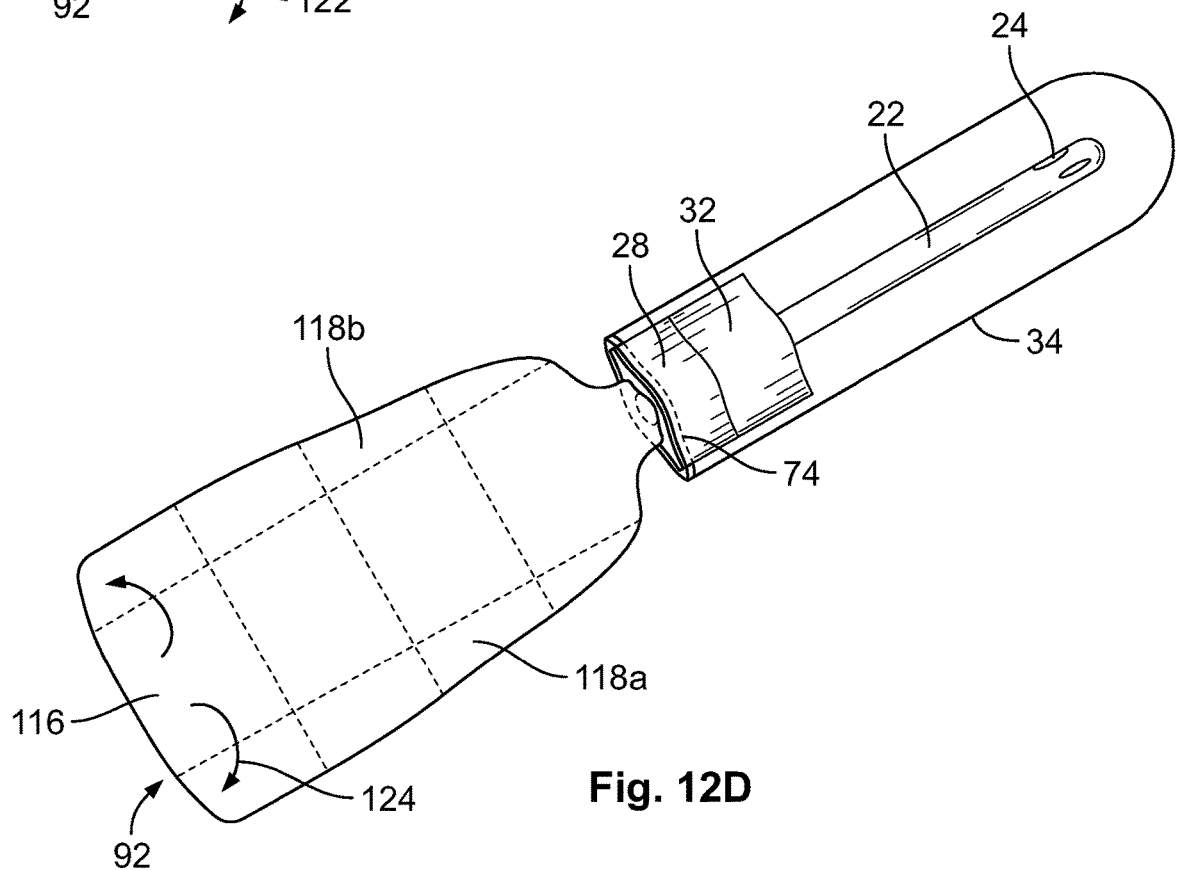

As illustrated in FIG. 12C, the collection bag 92 is folded so as to include a central portion 116 that is flanked by wing portions 118a and 118b. As illustrated by arrows 122 of FIG. 12C and arrows 124 of FIG. 12D, the wing portions of the collection bag are unfolded so that the collection bag is ready for use. The distal and proximal grip members 28 and 32 may then be pivoted or twisted with respect to one another so that the sleeve 34 is torn along tear line 74 and the catheter may be removed from the sleeve (as illustrated in FIGS. 9A-9C). The grip members may then be further twisted with respect to one another so that the handle valve is placed in the open configuration (for example, FIG. 7B or 8B) so that a urine stream may flow through the eyelets 24 and lumen of the catheter, through the distal and proximal grip members 28 and 32 and into the collection bag 92 during a catheterization procedure.

While the preferred embodiments of the disclosure have been shown and described, it will be apparent to those skilled in the art that changes and modifications may be made therein without departing from the spirit of the disclosure, the scope of which is defined by the appended claims.

What is claimed is:

1. A urinary catheter comprising:
   a. a shaft including a hydrophilic material and a distal end and a proximal end with a lumen running therebetween, said proximal end including an eyelet in fluid communication with the lumen;
   b. a handle attached to the distal end of the shaft, said handle including a first grip member and a second grip member configured so that said first grip member pivots relative to the second grip member; and
   c. a sleeve defining an interior chamber with said shaft positioned within the interior chamber, said sleeve sealed to the first grip member so that when the first grip member is pivoted, the sleeve is torn open.

2. The urinary catheter of claim 1 wherein the first grip member includes
   a first internal passage therethrough and the second grip member includes a second internal passage therethrough, said first or second internal passage in fluid communication with the lumen of the shaft and said first and second grip members configured so as to pivot relative to each other between a closed configuration, where the first and second internal passages are not in fluid communication, and an open configuration, where the first and second internal passages are in fluid communication.

3. The urinary catheter of claim 1 wherein the first grip member forms a distal portion of the handle and the second grip member forms a proximal portion of the handle.

4. The urinary catheter of claim 1 wherein the first grip member pivots about a longitudinal axis of the shaft.

5. The urinary catheter of claim 1 wherein the second grip member is secured to the shaft in a fixed fashion.

6. The urinary catheter of claim 1 wherein the second grip member is pivotally mounted to the catheter.

7. The urinary catheter of claim 1 further comprising a collection bag attached to the catheter.

8. The urinary catheter of claim 7 wherein the collection bag is attached to the first grip member.

9. The urinary catheter of claim 8 wherein the collection bag includes a cylindrical connector that is secured to the first grip member.

10. The urinary catheter of claim 1 further including a hydration source positioned within the interior chamber of the sleeve.

11. The urinary catheter of claim 10 wherein the hydration source is liquid water in contact with the hydrophilic material.

12. The urinary catheter of claim 10 wherein the hydration source is a vapor hydration source.

13. A urinary catheter comprising:
   a. a shaft including a hydrophilic material and a distal end and a proximal end with a lumen running therebetween, said proximal end including an eyelet in fluid communication with the lumen;
   b. a handle attached to the distal end of the shaft, said handle including a first grip member with a first internal passage therethrough and a second grip member with a second internal passage therethrough, said first or second internal passage in fluid communication with the lumen of the shaft and said first and second grip members configured so as to pivot relative to each other between a closed configuration, where the first and second internal passages are not in fluid communication, and an open configuration, where the first and second internal passages are in fluid communication; and
   c. a sleeve including a sealed interior chamber with said shaft positioned within the interior chamber, wherein the sleeve is sealed to the first grp member so that the sleeve tears open when the first grip member is pivoted.

14. The urinary catheter of claim 13 further comprising a collection bag attached to the catheter.

15. The urinary catheter of claim 13 wherein the first grip member forms a distal portion of the handle and the second grip member forms a proximal portion of the handle.

16. The urinary catheter of claim 13 wherein the first grip member pivots about a longitudinal axis of the shaft.

17. The urinary catheter of claim 13 wherein the second grip member is secured to the shaft in a fixed fashion.

18. The urinary catheter of claim 13 wherein the second grip member is pivotally mounted to the catheter.

19. The urinary catheter of claim 14 wherein the collection bag is attached to the first grip member.

20. The urinary catheter of claim 19 wherein the collection bag includes a cylindrical connector that is secured to the first grip member.

21. The urinary catheter of claim 13 further including a hydration source positioned within the interior chamber of the sleeve.

22. The urinary catheter of claim 21 wherein the hydration source is liquid water in contact with the hydrophilic material.

23. The urinary catheter of claim 21 wherein the hydration source is a vapor hydration source.

* * * * *